United States Patent [19]

Nickisch et al.

[11] Patent Number: 4,871,482
[45] Date of Patent: Oct. 3, 1989

[54] PROCESS FOR THE PREPARATION OF 1-METHYLANDROSTA-1,4-DIENE-3,17,DIONE, AND THE NOVEL INTERMEDIATES FOR THIS PROCESS

[75] Inventors: Klaus Nickisch; Hanfried Arnold, both of Berlin, Fed. Rep. of Germany

[73] Assignee: Schering Aktiengesellschaft, Berlin and Bergkamen, Fed. Rep. of Germany

[21] Appl. No.: 190,977

[22] Filed: May 6, 1988

[30] Foreign Application Priority Data

May 7, 1987 [DE] Fed. Rep. of Germany ....... 3715869

[51] Int. Cl.⁴ ................................................. C07J 1/00
[52] U.S. Cl. ................................ 260/397.3; 260/397.4
[58] Field of Search ............................... 514/177, 178; 260/397.3, 397.4

[56] References Cited

U.S. PATENT DOCUMENTS

| 3,134,792 | 5/1964 | Kaspar et al. | 260/397.3 |
| 3,758,523 | 9/1973 | Philippson et al. | |
| 4,591,585 | 5/1986 | Kerb et al. | 514/177 |

FOREIGN PATENT DOCUMENTS

| 3338212 | 10/1983 | Fed. Rep. of Germany | 514/177 |
| 3322285 | 12/1984 | Fed. Rep. of Germany | 260/397.3 |
| 2177700 | 1/1987 | United Kingdom | 260/397.3 |

OTHER PUBLICATIONS

J. Am. Chem. Soc. 82, pp. 5488 to 5493 (1960).

Primary Examiner—Douglas W. Robinson
Assistant Examiner—Joseph A. Lipovsky
Attorney, Agent, or Firm—Millen, White & Zelano

[57] ABSTRACT

1-Methylandrosta-1,4-diene-3,17-dione is prepared by a process wherein a 3-enol ester or 3-enol ether of general Formula II

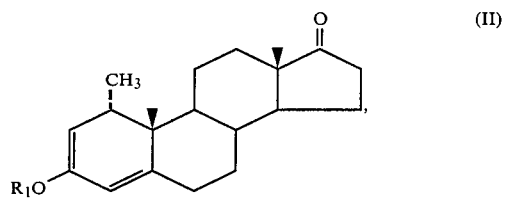

wherein
$R_1$ is an alkyl residue of 1–3 carbon atoms or an acyl or trialkylsilyl group of up to 10 carbon atoms in the group, is converted into the 2-bromo steroid of Formular III

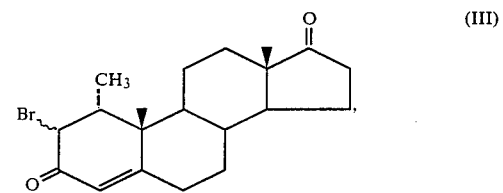

wherein the bromine substituent can be in the α- as well as in the β-position, and the compound of general Formula III is converted into 1-methylandrosta-1,4-diene-3,17-dione.

17 Claims, No Drawings

PROCESS FOR THE PREPARATION OF 1-METHYLANDROSTA-1,4-DIENE-3,17,DIONE, AND THE NOVEL INTERMEDIATES FOR THIS PROCESS

BACKGROUND OF THE INVENTION

This invention relates to a novel process for the preparation of 1-methylandrosta-1,4-diene-3,17-dione (Metandroden) and to the novel intermediates for this process. Metandroden is an inhibitor of estrogen biosynthesis (DOS No. 33 22 285; U.S. Pat. No. 4,591,585).

Heretofore, 1-methylandrosta-1,4-diene-3,17-dione has been prepared by oxidation of 17β-hydroxyl-1-methylandrosta-1,4-dien-3-one (DOS No. 33 22 285) or by microbiological dehydrogenation of 1-methyl-15α-andros-1-ene-3,17-dione (DOS No. 35 12 328). The preparation methods for these two compounds themselves proceed by way of multi-stage syntheses and in low yields.

A problem that has not as yet been solved satisfactorily is the introduction of the $\Delta^1$-double bond in the steroid having a 1α-methyl group and a $\Delta^4$-double bond.

Thus far, the 1-methylandrosta-1,4-diene-3,17-dione system has been produced from the corresponding 17β-hydroxyandrosta-1,4-dien-3-one via the synthesis sequence (a) copper-catalyzed organometal Michael addition of a methyl anion (DAS No. 20 46 640),
(b) hydrogenation of the $\Delta^4$-double bond to the corresponding 5α-H-compound,
(c) dibromination to the 2,4-dibromo steroid,
(d) dual hydrogen bromide elimination, and
(e) oxidation of the 17-alcohol to the 17-ketone (DOS No. 33 38 212 and DOS No. 35 39 244).

In this way of performing the synthesis, the already present $\Delta^4$-double bond is hydrogenated (blocking group effect) and thereafter reintroduced together with the $\Delta^1$-double bond.

This cumbersome process must be utilized because within the purview of the state of the art there is no suitable process known for evolving the 1-methylandrosta-1,4-diene-3,17-dione system directly from a 1α-methyl-4-androstene-3,17-dione.

The synthesis in accordance with the above-described synthesis sequence is furthermore made difficult by purification problems at the stage of dual hydrogen bromide elimination. The 2,4-dibromo-17β-hydroxy-1α-methyl-5α-H-androstan-3-one reacts under the reaction condition to yield in addition to the desired 17β-hydroxy-1-methylandrosta-1,4-dien-3-one, also the undesirable 17β-hydroxy-1α-methylandrosta-4,6-dien-3-one in equal yields [J. Am. Chem. Soc. 68:1712 (1946) and Coll. Czech. Chem. Comm. 26:1852 (1961)]. This undesired by-product can be separated (chromatography) only with difficulties due to its similar properties.

SUMMARY OF THE INVENTION

It has now been found that 1-methylandrosta-1,4-diene-3,17-dione can be prepared by following a shorter synthesis route without expensive chromatographic purification procedures and in a higher total yield. A simpler process has been developed for the bromination and dehydrobromination after converting the androstane-1,4-diene-3,17-dione into the 3-enoloxy-1α-methylandrosta-2,4-dien-17-one, wherein at the same time the aforedescribed purification problems at the stage of dual hydrogen bromide elimination are abolished.

The starting material for the novel synthesis is the readily accessible androsta-1,4-diene-3,17-dione [J. Am. Chem. Soc. 79:3920 (1957), Tetrahedron 4:201 (1958)].

Accordingly, the invention concerns a process for the preparation of 1-methylandrosta-1,4-diene-3,17-dione of Formula I

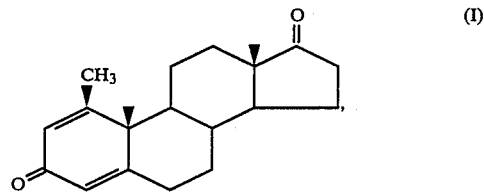

characterized in that a 3-enol ester or 3-enol ether of general Formula II

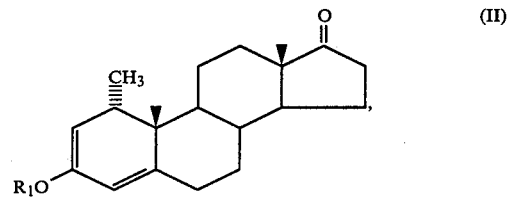

wherein $R_1$ is an alkyl residue of 1–3 carbon atoms or an acyl or trialkylsilyl group of up to 10 carbon atoms in the group, is reacted with elemental bromine or with a brominating reagent wherein the active bromine is present bound to amidic nitrogen, to obtain the 2-bromo steroid of Formula III

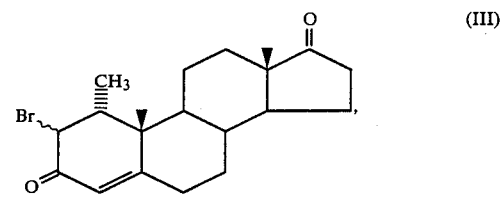

wherein the bromine substituent can be in the α- as well as in the β-position, and the compound of general Formula III is converted into the compound of general Formula I by dehydro-bromination in the presence of alkali or alkaline earth metal oxides or carbonates.

The invention furthermore relates to compounds of general Formulae III above and II

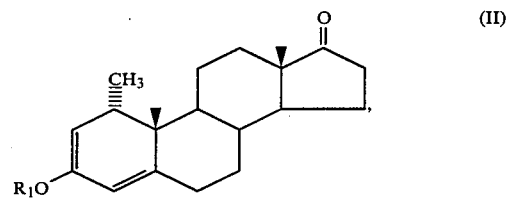

wherein $R_1$ is an alkyl residue of 1-3 carbon atoms or an acyl or trialkylsilyl group of up to 10 carbon atoms in the group, obtained as intermediate products of the process by reacting androsta-1,4-diene-3,17-dione with a methyl anion along the lines of a Michael addition, and subsequent scavenging of the enolate.

Suitable as the residue $R_1$ of general Formula II are alkyl residues of 1-3 carbon atoms, e.g., methyl, ethyl, n-propyl or iso-propyl, or acyl, e.g., alkanoyl, or trailkylsilyl residues of up to 10 carbon atoms in the overall group. Especially suitable are acetyl or trimethylsilyl. Alkanoyl includes acyl groups wherein the alkyl portion is methyl, methyl, n-propyl, iso-propyl, or one of the isomers of butyl, pentyl, hexyl, heptyl, octyl, nonyl or decyl.

The compound of general Formula II is prepared from androsta-1,4-diene-3,17-dione by reaction with a methyl anion along the lines of a Michael addition wherein the enol, forming as the intermediate product, is scavenged as the enol derivative. Suitable methyl anions useful for the Michael addition (1,4-addition) can be formed selectively from a Grignard reagent in the presence of copper(I) salts, e.g., copper(I) iodide or bromide, or from an organo-copper lithium compound, for example, copper dimethyllithium.

To form the various $R_1$-bearing compounds, scavenging of the aforementioned enol is accomplished with orthoacetic acid trimethyl ester, triethyl ester, or tripropyl ester, or also with 2,2-dimethoxypropane, with the acid anhydrides or acid chlorides of the organic carboxylic acids with 1-10 carbon atoms, or with trimethylsilyl chloride, tribenzylsilyl chloride, dimethyl tert-butylsilyl chloride, etc., in inert solvents, such as, for example, dichloromethane, carbon tetrachloride, dimethyl sulfoxide or dimethylformamide. The alkyl groups on the silyl radicals can be substituted, e.g., with phenyl. Especially suitable alkyl groups are the trimethyl- and the dimethyl-tert.-butyl residues.

Copper dimethyllithium prepared in situ from copper(I) iodide and methyllithium in dichloroethane reacts on the steroid along the lines of a 1,4-addition. The thus-formed enolate is preferably scavenged as the enol acetate with acetic anhydride; 3-acetoxy-1α-methylandrosta-2,4-dien-17-one is obtained as a crystalline compound.

This derivative can be prepared solely by way of the aforedescribed reaction steps. In the reaction of the corresponding 3-keto-$\Delta^4$-derivative under the customary preparation methods for enol ethers and acylates [J. Am. Chem. Soc. 82:5488 (1960)] the product would not be the desired 2,4-dien-3-ol but rather the $\Delta^{3,5}$-dienol derivative [J. Org. Chem. 26:976 (1961)]. "For the Michael addition-type reaction, suitable solvents are those stated above, suitable reaction temperatures are $-78°-+20°$ C., suitable reaction times are 0,5-2 hours, and, normally, the amounts of reactants, based on the amount of starting material dione are 1-10 equivalents for the methyl anion reagent and 1-10 equivalents for the scavenging reagent. For the preparation of the methyl anion reagent, typical reaction times are 0,5-2 hours and reaction temperatures are $-78°-+20°$ C., relative proportions or reagents being 1-10 equivalents of copper-(I)-iodide and 0.5-5 equivalents of a methyl lithium solution (reference: DAS No. 20 46 640).

Introduction of the bromine atom in the 2-position of the steroid is obtained by conversion of compounds of general Formula II into compounds of Formula III by reaction with elemental bromine or with a brominating reagent wherein the active bromine is present bound to amidic nitrogen. Suitable brominating reagents include, for example, N-bromosuccinimide or 1,3-dibromo-5,5-dimethyl-hydantoin.

3-Acetoxy-1α-methylandrosta-2,4-dien-17-one yields, by bromination with 1,3-dibromo-5,5-dimethyl-hydantoin in aqueous dioxane, 2α-bromo-1α-methyl-4-androstene-3,17-dione containing a small amount of 2α-bromo-1α-methyl-4-androstene-3,17-dione. Other polar aprotic solvents are likewise suitable for the bromination, such as, for example, tetrahydrofuran, acetone, dichloromethane, or water. Also suitable are solvent mixtures of two or several components, such as, for example, the mixtures of dioxane/water (1:1); dioxane/acetone/dichloromethane (3:1:2); and tetrahydrofuran/dioxane/water (10:3:1). "In the bromination step, typical reaction times are 0,5-10 hours, rection temperatures are $-10°-+40°$ C. and relative proportions of reactants are, based on the starting material steriod, 1-10 equivalents of brominating reagent."

Splitting off hydrogen bromide to obtain the compound of general Formula I takes place from the bromine compound by treatment with an alkali or alkaline earth metal oxide or carbonate in dimethylformamide. The reaction proceeds especially well with magnesium oxide. Addition of the bromine compound is preferably effected into the preheated reaction mixture heated so that the reaction temperature does not fall below about 110° C. However, it is possible to work at temperatures higher than 110° C. up to the boiling temperature of dimethylformamide. Besides the desired 1-methylandrosta-1,4-diene-3,17-dione, only about 5% of 1α-methylandrosta-4,6-diene-3,17-dione is found in the reaction mixture. In addition to dimethylformamide, suitable solvents for the dehydrobromination are also dimethylacetamide, dimethylimidazolidinone, and dimethyl sulfoxide, by themselves, in a mixture with one another, or in a mixture with water. "For the dehydrobromination step, suitable reaction times are 0,5-10 hours and relative proportions of reactants are, based on the starting brominated steroid, 1-30 equivalents of alkali or alkaline earth metal compound." The desired 1,4-diene has been separated from the byproduct 4,6-dien only by recrystallisation.

In order to maximize yield, attention must be devoted to maintaining optimum splitting-off conditions, on account of the notorious migration tendency of the 2-bromo substituent to the 4- or 6-positions which would give rise to the formation of the $\Delta^{4,6}$-steroid [Coll. Czech. Chem. Comm. 26:1852 (1961)] and, thus, lowered yields. In the splitting-off conditions the optimum reaction temperatures are higher than 110° C. up to 160° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

3-Acetoxy-1α-methylandrosta-2,4-dien-17-one

A suspension of 15.38 g of copper(I) iodide in 50 ml of dichloroethane is cooled to -30° C., combined at this temperature with 100 ml of methyllithium solution and stirred for one hour. A solution of 12.8 g of androsta-1,4-diene-3,17-dione [J. Am. Chem. Soc. 79:3920 (1957); Tetrahedron 4:201 (1958)] in 60 ml of dichloroethane is added dropwise to this mixture in such a way that the temperature does not rise beyond $-10°$ C. After this addition is completed, the mixture is further stirred for 2 hours at 0° C. To this yellow-brownish solution, a solution of 8.62 g of acetic anhydride in 22 ml of dichloroethane is added and the mixture is stirred for one hour at room temperature. Then a solution of 8.3 g of ammonium chloride in 83 ml of water is added dropwise thereto. The organic phase is separated, the aqueous phase is extracted with methylene chloride and the combined organic phases washed with water. After drying over sodium sulfate, the mixture is concentrated under vacuum and the resultant crude product in recrystallized from hexane/acetone, thus obtaining 8.9 g of 3-acetoxy-1α-methylandrosta-2,4-dien-17-one, mp 104°–107° C.

EXAMPLE 2

2β-Bromo-1α-methyl-4-androstene-3,17-dione and 2α-Bromo-1α-methyl-4-androstene-3,17-dione Under ice cooling, a suspension of 5.18 g of 3-acetoxy-1α-methylandrosta-2,4-dien-17-one in 50 ml of dioxane and 100 ml of water is combined in portions with 2.2 g of 1,3-dibromo-5,5-dimethylhydantoin and stirred for one hour at room temperature. Subsequently, the mixture is precipitated into 1 liter of water saturated with sodium chloride, 2.7 g of sodium sulfite is added, and the mixture is stirred for 60 minutes. The precipitated residue is filtered off, washed free of chloride with water, and dried, thus obtaining 5.65 g of a mixture of 2β-bromo-1α-methyl-4-androstene-3,17-dione and 2β-bromo-1α-methyl-4-androstene-3,17-dione.

EXAMPLE 3

1-Methylandrosta-1,4-diene-3,17-dione

Five grams of a mixture of 2β-bromo- and 2α-bromo-1α-methylandrost-4-ene-3,17-dione is introduced into a suspension, preheated to 115° C., of 1 g of magnesium oxide in 30 ml of dimethylformamide so that the temperature does not drop below 110° C. Then the mixture is stirred into 300 ml of ice water, filtered, and dried. The resultant crude produce of 3.85 g is subsequently recrystallized from ethyl acetate/hexane, yielding 2.75 g of 1-methylandrosta-1,4-diene-3,17-dione, mp 165°–167° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of 1-methylandrosta-1,4-diene-3,17-dione of Formula I

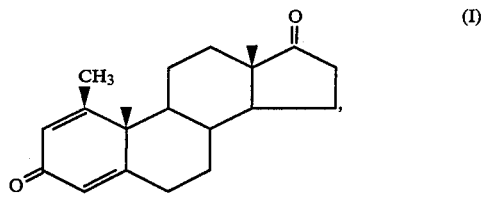

comprising reacting a 3-enol ester or 3-enol ether of Formula II

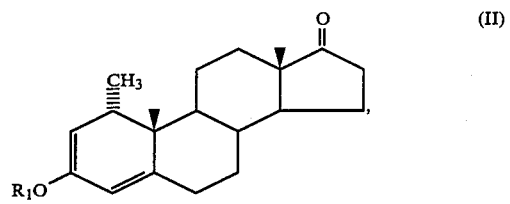

wherein $R_1$ is alkyl of 1–3 carbon atoms or alkanoyl or trialkylsilyl each of up to 10 carbon atoms in total with elemental bromine or with a brominating agent wherein the active bromine atom is present bound to amidic nitrogen, to obtain the bromo steroid of Formula III

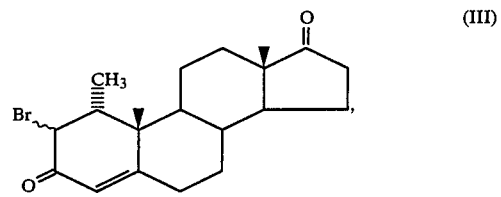

wherein the bromine substituent is in the α- or β-position, and dehydrobrominating the compound of Formula III in the presence of an alkali or alkaline earth metal oxide or carbonate to form the compound of Formula I.

2. A process of claim 1, wherein the bromination is conducted in a polar aprotic solvent or water.

3. A process of claim 2, wherein the solvent is dioxane, tetrahydrofuran, acetone, dichloromethane, or a mixture thereof.

4. A process of claim 1, wherein the dehydrobromination is conducted in a solvent which is selected from the group consisting of dimethylformamide, dimethylacetamide, dimethylimidazolidinone, dimethyl sulfoxide, water, and mixtures thereof.

5. A process of claim 1, wherein the brominating agent is $Br_2$, N-bromosuccinimide or 1,3-dibromo-5,5-dimethylhydantoin.

6. A process of claim 1, wherein $R_1$ is acetyl or trimethylsilyl.

7. A process of claim 1, wherein the dehydrobromination reagent is magnesium oxide.

8. A process of claim 1, wherein the dehydrobromination is conducted at a temperature above about 110° C.

9. A process according to claim 1, wherein the bromination step is carried out in 0.5 to 10 hours.

10. A process according to claim 9, wherein the bromination is conducted at a temperature of −10° to 40° C.

11. A compound of Formula II

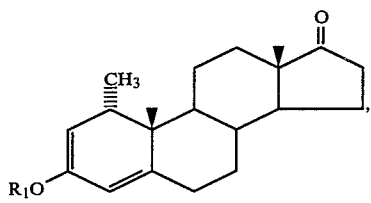

wherein
R₁ is alkyl of 1-3 carbon atoms, C₁₋₁₀-alkanoyl or trialkylsilyl of up to 10 carbon atoms in total.

12. A compound of claim 11 wherein R₁ is acetyl or trimethylsilyl.

13. 3-Acetoxy-1α-methylandrosta-2,4-dien-17-one, a compound of claim 11.

14. A compound of claim 11, wherein R₁ is methyl, ethyl, n-propyl, or iso-propyl.

15. 2α-Bromo-1α-methyl-4-androstene-3,17-dione.

16. 2β-Bromo-1α-methyl-4-androstene-3,17-dione.

17. A process for the preparation of a compound of Formula III

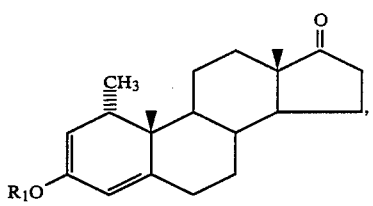

wherein
Br is in the α- or β-position, comprising reacting a 3-enol ester or 3-enol ether of Formula II

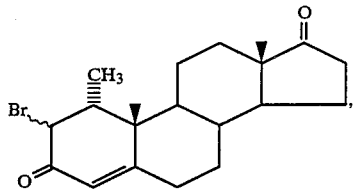

wherein
R₁ is alkyl of 1-3 carbon atoms or alkanoyl or trailkylsilyl each of up to 10 carbon atoms in total with elemental bromine or with a brominating agent wherein the active bromine atom is present bound to amidic nitrogen.

* * * * *